United States Patent [19]
Jacobsen et al.

[11] Patent Number: 4,886,489
[45] Date of Patent: Dec. 12, 1989

[54] FLOW-THROUGH METHODS AND APPARATUS FOR IONTOPHORESIS APPLICATION OF MEDICAMENTS AT A CONTROLLED PH

[76] Inventors: Stephen C. Jacobsen, 274 S. 1220 East, Salt Lake City, Utah 84102; Tomasz J. Petelenz, 623 University Village; Robert L. Stephen, 2501 Kensington Ave., both of Salt Lake City, Utah 84108

[21] Appl. No.: 64,813

[22] Filed: Jun. 19, 1987

Related U.S. Application Data

[63] Continuation-in-part of Ser. No. 841,329, Mar. 19, 1986, Pat. No. 4,752,285.

[51] Int. Cl.⁴ .............................................. A61N 1/30
[52] U.S. Cl. ...................................... 604/20; 128/783; 604/305
[58] Field of Search ................. 604/20, 289, 290, 294, 604/304, 305; 128/639, 640, 783, 798, 799, 802, 803

[56] References Cited

U.S. PATENT DOCUMENTS

| 2,126,070 | 8/1938 | Wappler | 604/20 |
| 3,623,479 | 11/1971 | Day | 128/639 |
| 3,991,755 | 11/1976 | Vernon et al. | |
| 4,140,130 | 2/1979 | Storm, III | 128/798 |
| 4,141,359 | 2/1979 | Jacobsen et al. | |
| 4,166,457 | 9/1979 | Jacobsen et al. | |
| 4,215,696 | 8/1980 | Bremer et al. | |
| 4,250,878 | 2/1981 | Jacobsen et al. | |
| 4,292,968 | 10/1981 | Ellis | |
| 4,383,529 | 5/1983 | Webster | |
| 4,416,274 | 11/1983 | Jacobsen et al. | 604/20 |
| 4,419,092 | 12/1983 | Jacobsen et al. | 604/20 |
| 4,465,074 | 8/1984 | Buchalter | 128/639 |
| 4,474,570 | 10/1984 | Ariura et al. | 604/20 |
| 4,477,971 | 10/1984 | Jacobsen et al. | |
| 4,526,176 | 7/1985 | Bremer et al. | 128/641 |
| 4,557,723 | 12/1985 | Sibalis | 604/20 |
| 4,570,637 | 2/1986 | Gomes et al. | 128/639 |
| 4,602,909 | 7/1986 | Csillik et al. | 604/20 |
| 4,639,244 | 1/1987 | Rizk et al. | 604/19 |
| 4,722,726 | 2/1988 | Sanderson et al. | 604/20 |
| 4,744,787 | 5/1988 | Phipps et al. | 604/20 |
| 4,747,819 | 5/1988 | Phipps et al. | 604/20 |

FOREIGN PATENT DOCUMENTS 182520 5/1986 European Pat. Off. .

OTHER PUBLICATIONS

Petelenz, T. J. et al., "Iontophoresis as a Potential Method of Insulin Administration," International Sym- (List continued on next page.)

Primary Examiner—C. Fred Rosenbaum
Assistant Examiner—Mario Costantino
Attorney, Agent, or Firm—Workman, Nydegger & Jensen

[57] ABSTRACT

Methods and apparatus for administering known quantities of medicaments by iontophoresis, while avoiding burns caused by extremes in the pH of the medicament medium during passage of an electric current, are disclosed. It is known that as iontophoresis progresses in conventional iontophoresis systems, the electrolysis of water occurs to produce hydrogen or hydroxyl ions at the interface of the electrode and medicament medium. Since these ions are highly mobile, they are transported directly into the skin of a patient in preference to the larger medicament ions. Thus, extreme changes in pH are experienced which result in burns due to the acidification or alkalinization of the medicament medium and passage of electric current through the skin. In addition, the efficiency of iontophoresis decreases over time. The present invention avoids extremes in pH by removing the hydrogen or hydroxyl ions which are created during iontophoresis and creates conditions for constant delivery over prolonged periods of time.

In the present invention, the medicament medium adjacent the patient is periodically or constantly replaced by adding fresh medicament medium which is at the original pH. The present invention also discloses a flow-through electrode which allows new solution to constantly flow into the iontophoresis area.

11 Claims, 3 Drawing Sheets

OTHER PUBLICATIONS posium on Artificial Organs, Biomedical Engineering and Transplantation, p. 6 (Jan. 20-23, 1986).

Phipps, J. B., et al., "Evaluation of Transdermal Iontophoretic Drug Delivery," International Symposium on Artificial Organs, Biomedical Engineering and Transplantation, p. 7 (Jan. 20-23, 1986).

Molitor et al., "Studies on Iontophoresis: I. Experimental Studies on the Causes and Prevetion of Iontophoretic Burns," American Journal of Medical Science, vol. 198, pp. 778-785 (Dec. 1939).

Molitor, H., "Pharmacologic Aspects of Drug Administration by Ion-Transfer," The Merck Report, pp. 22-29 (Jan. 1943).

Abramowitz, "Ion Transfer or Iontophoresis," Galvanic Current, pp. 120-124.

Waud, D., "Ionophoretic Application of Drugs," Journal of Applied Physiology, vol. 23, pp. 128-130 (Jul. 1967).

Boone, D., "Hyaluronidase Iontophoresis," Physical Therapy, vol. 49, pp. 139-145 (1968).

Gore et al., "A Capacitive-Discharge, Microiontophoretic Device with Single-Ended Output," Journal of Applied Physiology, vol. 30, pp. 264-267 (Feb. 1971).

Spencer, H., "Programmable Nanoampere Constant Current Sources for Iontophoresis," Medical and Biological Engineering, vol. 9, pp. 693-702 (Nov. 1971).

Handbook of Physical Medicine and Rehabilitation, Second Edition, Krusen et al., editors, pp. 379-380 (1971).

Geller et al., "An Improved Constant Current Source for Microiontophoretic Drug Application Studies," Electroencephalography and Clinical Neurophysiology, vol. 33, pp. 430-432 (1972).

Bloom, F. E., "To Spritz or Not to Spritz: The Doubtful Value of Aimless Iontophoresis," Life Sciences, vol. 14, pp. 1819-1834.

Johnson et al., "On the Safe Electrical Administration of Ionized Drugs/Iontophoresis," 30th ACEMB, Los Angeles, California, (Nov. 5-9, 1977).

"Painless Anesthesia Device Developed by U Researchers," Health Sciences Report, p. 5, (Jan. 1978).

Langley, "Iontophoresis to Aid in Releasing Tendon Adhesions," Physical Therapy, vol. 64, No. 9, p. 1395 (Sep. 1984).

Shaya et al., "Percutaneous Electrophoresis of Amino Acids and Urea," Medical and Biological Engineering and Computing, vol. 16, pp. 126-134 (1978).

"Ionotophoresis," Medical Electronics, pp. 174 and 175 (Feb. 1984).

Phipps, J. B., et al., "Evaluation of Transdermal Iontophoresis Drug Delivery," International Symposium on Artificial Organs, Biomedical Engineering and Transplantation (Jan. 20-23, 1986).

FLOW-THROUGH METHODS AND APPARATUS FOR IONTOPHORESIS APPLICATION OF MEDICAMENTS AT A CONTROLLED PH

BACKGROUND

1. Related Application

This application is a continuation-in-part application of our copending application Ser. No. 841,329, filed March 19, 1986, now U.S. Pat. No. 4,752,285 entitled METHODS AND APPARATUS FOR IONTOPHORESIS APPLICATION OF MEDICAMENTS, which application is incorporated herein by this reference.

2. The Field of the Invention

This invention relates to methods and apparatus for administering substances by iontophoresis. More particularly, the present invention discloses methods and apparatus for administering determinable quantities of medicaments and the like by iontophoresis in a safe and efficient manner using a flow through electrode.

3. The Background of the Invention

The process of iontophoresis was reported as early as about 1740 for use in applying medication locally through a patient's skin and later in about 1900 for use in delivering medicaments to the eyes and ears as well. In its simplest terms, this technique involves the application of an electromotive force to drive ionic chemicals through the skin so that they can be absorbed by the adjacent tissues and blood vessels. By iontophoresis techniques, various substances (including some pharmaceuticals and medicaments) have been administered to a patient without the necessity of a hypodermic injection and without the associated problems, such as pain, the risk of infection, and trauma to the patient.

While iontophoresis has been the subject of continuous experimentation for many years, the process has not been used to any major extent by medical practitioners. Iontophoresis has been tested for use in treatments such as the application of local anesthetics, the application of medication for treatment of skin disorders, and the application of other limited types of medications in order to achieve a localized effect.

As mentioned above, iontophoresis involves the application of an electromotive force to drive ions through the skin. Accordingly, ions bearing a positive charge are driven into the skin at the anode of an electrical system, and ions bearing a negative charge are driven into the skin at the cathode of the electrical system. For example, positively charged ions such as zinc, copper, alkaloids, certain anesthetics, and certain vasodilating drugs are introduced into the skin or the mucous membranes from the positive pole. On the other hand, a negatively charged drug, such as salicylate, fluoride, penicillin, and insulin can be driven into the skin using the negative pole.

Some drugs have exhibited their effect at the site of iontophoresis, where they are initially introduced through the skin. Examples of such drugs which exhibit localized effects upon iontophoresis through the skin are local anesthetics.

Various other drugs can be administered to exhibit systemic effects by iontophoretically driving the drug into the circulatory system. In such cases, the ions transferred through the skin are absorbed into the blood stream and enter the body's general blood circulatory system.

Iontophoretic delivery of medicaments can provide significant benefits over other methods of delivery. For example, when a medicament is taken orally, it must be absorbed through the digestive tract. However, uptake of the medicament through the digestive tract varies greatly from individual to individual. Moreover, the drug must pass through the liver where it is not unusual for upwards of 70% of the drug to be inactivated on the first pass through the liver.

Thus, because a medicament delivered iontophoretically can be quickly absorbed into the circulatory system, iontophoresis is capable of avoiding the "first pass effect" in the administration of certain medicaments. In addition, patient discomfort and noncompliance, and the risk of infection associated with injections are also eliminated when using iontophoresis.

While iontophoresis has been applied to many different drugs, it has never established itself as a widely used method for the delivery of medicaments. This was partly caused by the use of poor equipment and the lack of understanding of the mechanism of iontophoresis and its potential safety hazards. This historic view of iontophoresis, however, began to change somewhat in about 1959.

At that time, a test was devised, using iontophoresis, to diagnose cystic fibrosis. It was found that pilocarpine could be iontophoretically administered onto localized areas of skin so as to induce sweating. The sweat could then be collected and tested for abnormal levels of sodium or chloride, which is diagnostic of cystic fibrosis. This technique met with approval and was eventually selected by the Cystic Fibrosis Foundation as the standard and only acceptable test for diagnosing cystic fibrosis.

The widespread use of iontophoresis in diagnosing cystic fibrosis has resulted in some noticeable improvements in the equipment used to supply electrical current and in the electrodes used in iontophoretic applications. This use of iontophoresis has also led to some additional understanding of the mechanisms involved in iontophoresis. However, outside the field of cystic fibrosis diagnosis, the technique has yet to receive widespread acceptance.

Notwithstanding the limited acceptance of iontophoresis, the potential uses of iontophoresis can be readily appreciated from the previous discussion. Iontophoresis can obviously be used to introduce medicaments and other substances into the body without the necessity of an injection. Its use could thus become extremely significant in administering drugs and pharmaceuticals where frequent injections are required.

Specifically, the primary application of iontophoresis has been for administration of locally acting medications, i.e., resulting in negligible systemic concentration and thus greatly reduced toxicity. It has been acknowledged, that electrochemical reactions occurring at the electrodes cause adverse reaction of the skin and preclude extended application time required to achieve prolonged systemic effects.

Frequent injections over a prolonged period of time as a form of treatment has several disadvantages. Many individuals find it difficult to adjust to the requirement of multiple daily injections, which are painful, carry the risk of infection, and cause additional strain on their already taxed system, possibly modifying the effects of the drug.

Iontophoresis as an alternative to existing methods of systemic administration of medicaments has several advantages. The use of iontophoresis to administer such substances results in a high percentage of the substance actually reaching the systemic circulation—this is in direct contrast to oral administration where the drug is subject to the irregularities of the digestive process and possible inactivation by the liver prior to being absorbed into the systemic circulatory system. As a result, a relatively large quantity of a drug must be ingested orally in order to obtain the desired concentration of the drug in the bloodstream and to achieve the desired therapeutic effect. It will be appreciated that since each patient's digestive system functions differently, the amount of an orally ingested drug needed to achieve the desired therapeutic effect is often difficult to predict.

Another potential advantage of iontophoresis is the ability to administer medicaments over a sustained period of time without invasion of the body. Optimally, it is often desirable to maintain a certain constant level of medicament within the patient's system, instead of periodically injecting a bolus of medicament. However, due to limitations in the presently available iontophoresis systems, this sustained delivery is not practical because of the danger of electrical and chemical burns to the patient.

While the use of iontophoresis has many potential benefits, traditional iontophoretic techniques have suffered several drawbacks such that the iontophoretic administration of medicaments has not been generally very practical. In particular, traditional techniques for iontophoresis have been considered unsafe, unpredictable, inconvenient, or uneconomical. It is for these reasons that iontophoresis has not enjoyed widespread acceptance in the medical field. Moreover, due to the short duration of administration, iontophoresis has been almost exclusively used to administer locally active medicaments.

With respect to safety, it is found that iontophoresis may result in burns to the patient's skin. These burns stem from two sources: (1) galvanic sources where the electrical current itself causes burns, and (2) chemical sources where extremes in pH (which develop during the iontophoresis process) act in conjunction with electric current to result in chemical burns.

Methods and procedures have been developed to control serious galvanic burns and other electrical hazards. For example, it has been suggested that the electrical current used in the iontophoretic process be increased slowly and that limitations be placed on the amount of current delivered.

Galvanic burns can also be minimized or reduced by keeping the current density per unit area of skin below threshold values at which burning begins. Low current densities can be achieved by attention to techniques of iontophoresis, such as avoiding folds or wrinkles between the electrode and the skin (whih cause high localized current density resulting in burns), using a gel-moistened electrode pad in connection with the electrode, and moistening the skin prior to and during iontophoresis. A further suggestion in the art has been to increase the surface area of the electrode so that the current is spread over a large area, thereby reducing current density. See U.S. Pat. No. 4,416,274 (Jacobsen et al.) entitled "Ion Mobility Limiting Iontophoretic Bioelectrode," and U.S. Pat. No. 4,477,971 (Jacobsen et al.) entitled "Iontophoretic Electrode Structure."

It is more difficult to control pH and the resulting burns caused by extremes in the alkalinity or acidity of the medicament solution during passage of electric current. As the current passes between the electrode contact and the medium containing medicament, there is increased production of hydrogen ions ($H^+$) or hydroxide ions ($OH^-$). This increase in concentration is caused by the exchange of charge through the electrolysis of water.

Since the $H^+$ and $OH^-$ which result from the electrolysis of water are significantly more mobile than most of other ions, they migrate rapidly through the solution away from the electrode and toward the skin of the patient. Thus, an area of extreme pH is ultimately created directly adjacent to the skin. This area of extreme pH is clearly dangerous and has been observed to cause serious burns when the current causes these ions to pass through the skin. Thus, the changes in pH has imposed a time limit on the duration of prior art iontophoretic treatments, usually limited to only about twenty (20) to thirty (30) minutes per treatment.

Attempts have been made to control pH in the iontophoretic system. Heretofore, these attempts have been less than satisfactory. One method of attempting to control pH has been to introduce a buffer into the iontophoretic system. The introduction of buffers, however, is found to defeat some of the important useful features of iontophoresis.

The introduction of buffers results in increasing concentrations of additional ionic species within the system. In a solution containing a mixture of ions, the quantity of a specific ion that will be moved by a given electromotive force is proportional to (a) the concentration of the ion, (b) the mobility of the ion, and (c) the valence charge on the ion.

Typically, the buffer ions which, are usually small and very mobile (such as phosphate ions, and complementary cations such as sodium), will migrate through the solution at a much faster rate than will the larger ions (such as drug molecules) which are the medicament ions to be transported through the skin of the patient by the iontophoretic process. The result is that a large percentage of buffer ions may be driven into the skin by iontophoresis instead of the desirable medicament ions. Thus, the quantity of medicament molecules driven through the skin is seriously reduced and the quantity of undesirable ions driven through the skin is increased.

Moreover, as would be expected from the foregoing, the use of buffers aggravates the problem of quantification of the amount of medicament delivered in any given iontophoretic administration. If buffer ions are forced through the skin, it will be difficult or impossible to determine how much of the medicament has passed through the skin. This is particularly true since most medicament ions, especially drug ions, are larger and therefore, slower in the electrical field created during the iontophoresis process than are the smaller buffer ions.

The existing literature has pointed out that administration of substances by ion transfer long has been regarded as one of the least accurate methods of administration. Indeed, the lack of accurate quantification techniques has been, and still is, one of the major objections to wide acceptance of iontophoresis.

A further problem encountered in the clinical use of iontophoresis is that iontophoresis systems have not been particularly convenient or economical. Generally, other methods of administration of medicaments have been less expensive and easier to use. Considerations of cost and convenience have, therefore, also impeded the general acceptance of iontophoresis.

As can be appreciated from the above discussion, the technique of iontophoresis has several major potential benefits for use in the medical area. Iontophoresis offers a technique whereby medicaments may be noninvasively introduced into the body. That is, the patient may receive a needed medication without the necessity of an injection of a bolus of medicament and without the unknowns associated with the "first pass effect" of oral administration. Moreover, iontophoresis has the potential of providing a method whereby continuous, sustained doses of medications may be administered.

Despite this potential for iontophoretic administration techniques, the present state of iontophoresis is such that it is not particularly safe, since both galvanic and pH-induced burns are common. While galvanic burns can, to a certain extent, be controlled by appropriate techniques known in the art, pH-related burns associated with the passage of electrical current through the solution remain problematic. These burns are painful and difficult to heal.

In addition, existing methods and apparatus do not provide for adequate quantification of the medicament being administered. This is caused in large measure by the $H^+$ and $OH^-$ produced during iontophoresis. These highly mobile ions compete with the larger, less mobile medicament molecules for introduction in the patient, thereby resulting in an inability to determine how much of the medicament actually reaches the patient. At the same time, iontophoresis has not traditionally been particularly economical or convenient.

Thus, what is needed in the art are techniques for iontophoretically administering medicaments and other substances to the body in such a manner that burns and other safety hazards to the patient are avoided. It would be a significant advancement to provide improved methods and apparatus for administration of a medicament using iontophoresis which would allow the amount of the medicament administered to be better quantified, controlled, and delivered for prolonged time periods (i.e., over a period of hours or even days).

It would be a further significant advancement in the art to provide such methods and apparatus for administering medicaments by iontophoresis which could operate safely without the addition of buffering ions. It would also be a significant advancement in the art if methods and apparatus could be provided for iontophoretic administration of medicaments which provided for close control of pH within the system. It would be still another advancement in the art to provide methods and apparatus for administration of medicaments using iontophoresis which are economical and convenient to use. Such methods and apparatus are disclosed and claimed herein.

BRIEF SUMMARY AND OBJECTS OF THE INVENTION

The present invention is related to methods and apparatus for safely administering known quantities of medicaments (such as drugs, pharmaceuticals, or other substances) to a patient using an iontophoretic process. Furthermore, the iontophoretic technique of the present invention maintain safe pH levels without the addition of buffering ions and minimize the introduction into the solution of ions which compete with the ionic medicaments for transference through the skin.

The electrolysis reaction of water will occur at the positive electrode when the potential between the aqueous solution and the electrode exceeds approximately +1.23 volts versus a Standard Hydrogen Electrode (hereinafter sometimes referred to as "SHE"). Electrolysis of water occurs at the negative electrode when the potential between the aqueous solution and the electrode exceeds approximately −0.83 volts vs. SHE. The direct consequence of the electrolysis of water is strong acidification at the positive electrode and strong alkalinization at the negative electrode.

The goal of preventing extremes in pH because of the electrolysis reaction of water may be achieved by introducing the medicament ion through the use of a flow-through system. Essentially, the medicament solution between the iontophoresis electrode and the patient is constantly flowing. As old solution flows out of the system it is replaced by a fresh solution of medicament. As a result, any undesirable ions produced during the iontophoresis procedure are removed as the old solution flows out of the electrophoresis system.

Using such a flow-through system, pH can be maintained within desirable limits without the necessity of adding a buffer. This is true because produced ions which cause extremes in pH ($H^+$ and $OH^-$) are constantly carried out of the system.

At the same time it is possible to quantify the amount of medicament carried through the iontophoresis system. This is true because essentially only medicament ions are carried by the current in the system. This is true even though the solution is constantly flowing.

It is, therefore, a general object of the present invention to provide improved methods and apparatus for the use of iontophoresis which are safe and which allow the amount of the medicament introduced to a patient to be more accurately quantified.

Accordingly, it is an object of the present invention to provide improved methods and apparatus for the use of iontophoresis which provide for close control of the pH of the iontophoretic system to avoid burns caused by changes in pH concentration on or near the skin of the patient and to prolong treatment time during the iontophoresis process.

It is another object of the present invention to provide such an iontophoresis system which controls the pH of the medicament medium without the use of buffers.

It is another object of the present invention to provide a flow-through iontophoresis system which removes any undesirable ions as they are produced.

It is also an object of the present invention to provide improved methods and apparatus for the use of iontophoresis which are simple, convenient and economical to use.

These and other objects and advantages of the invention will become more fully apparent from the following description and appended claims.

DETAILED DESCRIPTION OF THE PREFERRED EMBODIMENTS

A. The Mechanism of Iontophoresis

As discussed above, iontophoresis is found to be a promising method of introducing drugs and other similar substances into a patient. In particular, iontophoresis provides for the efficient delivery of drugs without invading the body. In the past, however, iontophoresis has not been widely accepted because of the inability to produce a system which was safe, quantifiable, economical, and convenient.

One of the most serious problems prohibiting the widespread clinical use of iontophoresis is the production of painful burns on the skin of the patient after only a short period of iontophoresis. In existing iontophoretic systems for current densities of approximately 0.5 mA/cm$^2$, changes in the skin are typically observed within the first five minutes of iontophoresis, and burns often occur when the process continues for thirty minutes or more depending on a total volume of an electrode. These burns are difficult to heal and may not be fully manifest until after the treatment has been completed.

The more difficult type of burns to eliminate are burns caused by extreme changes in pH of the iontophoresis solution, or iontophoresis medium, on or near the skin of the patient during passage of an electric current. In particular, electrical current flowing through an aqueous iontophoresis medium, which would typically be used where a medicament is being iontophoresed into a patient, produces a large quantity of $H^+$ or $OH^-$ ions.

These ions ($H^+$ or $OH^-$) move rapidly in response to the electromotive forces existing within the iontophoresis system because of their large electrophoretic mobility. Thus, when these ions are produced in the iontophoresis process, they are rapidly driven into the patient's skin causing localized extremes in pH. Such localized extremes in pH result in burns on the skin of patients.

Figure 1:
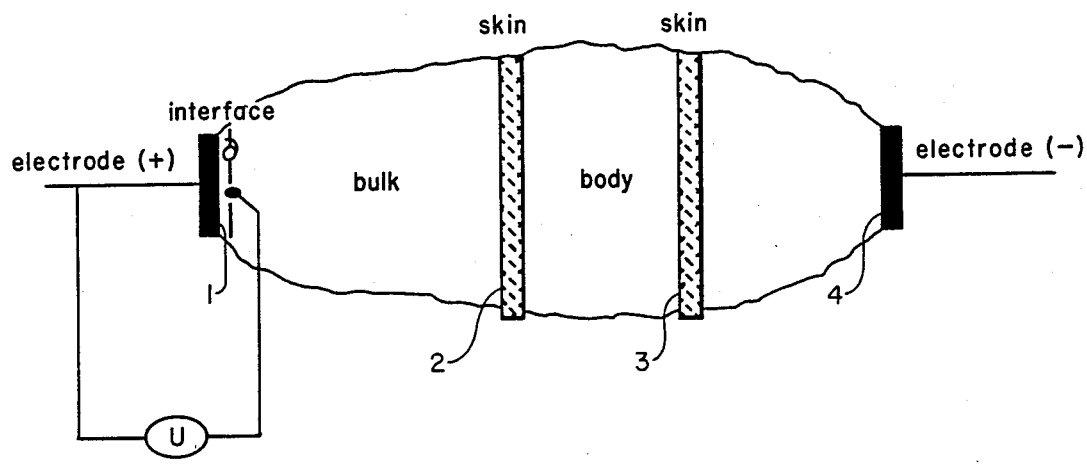
FIG. 1 is a schematic diagram of a general iontophoresis system which is within the scope of the present invention.

By definition, iontophoresis involves the transport of ions such as medicament ions, across a barrier such as the skin. The basic iontophoresis process can be clearly understood by reference to the schematic diagram of an iontophoretic system illustrated in FIG. 1. FIG. 1 illustrates the positive and negative electrode positioned on opposite sides of the body of the patient. Between the electrodes and the patient is a quantity of iontophoresis medium. By this orientation, a serious of interfaces is presented.

As seen in FIG. 1, these interfaces include the electrode medium interface between the anode and the adjacent medium (generally designated at 1), the medium-skin interface (generally designated at 2) between the iontophoresis medium on the anode side of the system and the patient, a similar medium-skin interface on the cathode side (generally designated at 3), and finally the medium-cathode interface (generally designated at 4).

It will be appreciated that there will be a voltage differential across each of these interfaces, since each interface will present an additional resistance. Moreover, because for a constant current voltage is directly proportional to resistance, the additional resistance of each interface results in a greater voltage differential between the two electrodes.

However, the total voltage drop across these interfaces is not necessarily directly related to the charge transfer in the system or the amount of medicament which is transferred to the patient. As will become evident, the amount of medicament transferred depends upon both the amount of current flow and the number and characteristics of the ions which compete with the medicament ion.

The present discussion will focus on methods and apparatus for exchanging desirable medicament ions with undesirable species produced during iontophoresis.

B. The Production and Effects of $H^+$ and $OH^-$

It will be appreciated that transportation of ions takes place in an electrical field such as that produced by the system illustrated in FIG. 1. Accordingly, the medicament to be delivered to the patient must exist in the system as an ion carrying an electrical charge. Since various compounds (such as salts, bases, or acids) dissociate upon dissolution in a solvent into two components, one positive and one negative, the medicaments used in iontophoresis are in the form of ions.

Thus, one of the components in the iontophoresis solution will be an ion which is the active portion of the medicament and the other component will be either a complementary ion, or in the case of certain embodiments of the present invention, a vacated active site in an ion exchange matrix. These charged ions are then subject to the electromotive forces exerted by the electrical field during iontophoresis such that the electrical field propels the ions through the system.

During iontophoresis, the medicament ions are attracted to the electrode having the opposite charge. This transportation of ions takes place in proportion to the product of the concentration, the mobility, and the charge (or valence) of the ions in solution. The fraction of total current carried by a particular ion species which determines the amount of transported drug, is called the transference number. The transference number for an ion k is expressed by Equation (1) which follows:

$$|z_k| \, _k C_k^{l_k} \, (|z_i| \, _i C_i) \qquad (1)$$

where:
$t_k$ is the transference number of ion k,
$z_k$ is the valance of ion k,
$u_k$ is the mobility of ion k,
$C_k$ is the concentration of ion k,
i is summation index
and summation is for all ions in the solution.

From Equation (1), it can be seen that as additional species are added to the system, the amount of drug, represented by ion k, transported during iontophoresis decreases for every additional species in solution. From the foregoing, it is readily apparent why the use of buffers and the like to control pH have been found to be unsatisfactory—the addition of the new species of the buffer or increase of concentration of any ion in the solution, correspondingly decrease the transport of the medicament.

In order to cause the medicament to move in the system at all, it is necessary to provide a driving force. In the case of iontophoresis, the driving force is an electrical potential difference. In order to cause current flow through the drug solution, it is necessary to provide a mechanism for charge exchange between the contact material of the electrode (typically a metal) and the electrolyte in the medium.

There are two types of electrodes which can be used for introducing a current through the iontophoresis system. These electrodes can generally be considered either "inert" or "reactive." The development of "reactive" electrodes is very new and is described in greater detail in our copending application identified above. For the purposes of the present discussion, however, an inert electrode will be presumed.

An "inert" electrode, is defined as an electrode at which the charge is exchanged with the solution according to the reaction of the electrolysis of water, as represented here at th positive pole, in Equation (2):

at $V \geq 1.23V$ (at the positive pole) vs. SHE, where $e^-$ is the electron charge.

According to Equation (2), the electrolysis of water occurs if the voltage between the solution adjacent to the anode and the material of the anode exceeds approximately 1.23 volts vs. SHE. (It will be appreciated that the precise voltage for the electrolysis of water will be dependent upon the pH and the temperature of the solution, as well as certain other parameters; however, the value of approximately $+1.23$ volts vs. SHE is used as a typical reference value which would be encountered under typical conditions.) Thus, if the voltage at the interface of the electrode and the medicament medium exceeds the electrolysis voltage of water, $H^+$ and $OH^-$ will be formed.

The consequence of the reaction of Equation 2, as can be appreciated from the products of the reaction, is rapid acidification of the medium. The hydrogen ions produced are transported rapidly from the medium-electrode interface through the medium to the medium-skin interface, thereby resulting in acidification and contributing to burning of the skin.

While the above reaction is specific for the positively polarized electrode, it will be appreciated that a similar reaction takes place at the negative electrode where the product of the reaction is the hydroxyl ion. This reaction occurs at a voltage of approximately $-0.83$ volts (vs. a Standard Hydrogen Electrode) between the medium and the cathode. This, of course, creates alkalinization of the medium and tissues by the same general mechanism that acidification occurs at the positive electrode. The result, however, is the same since alkalinization can also cause burns to the patient during passage of an electric current. As can be appreciated from formula (1) transference number for any ion k decreases upon introduction of additional hydrogen or hydroxyl ions.

Also the evaluation of the transference numbers reveals that due to the introduction of $H^+$ or $OH^-$ ions into the medium during iontophoresis, the fraction of the current transported by the medicament ions does not necessarily remain constant; in fact, the amount of current transported by the medicament ions may be significantly variable over time during iontophoresis. The consequence is that the actual rate of administration of the medicament to the patient may not, and generally, will not remain constant over time.

Thus, when concentrations of $H^+$ or $OH^-$ increase there is a corresponding reduction in the amount of drug transported through the skin of the patient. The result is that the dosage of the medicament delivered cannot be accurately quantified. Moreover, the potential effective treatment time is markedly reduced because of these factors.

C. Flow-Through Iontophoresis Electrode

The present invention discloses the introduction of medicament to the iontophoresis system by use of a flow-through electrode. A flow-through electrode is one in which the solution or other medium containing medicament is constantly flushed and replaced.

Employing such a flow-through electrode fresh solution is introduced to the region between the source of current and the patient at one location. At a separate location existing solution is removed. Thus, a constant supply of fresh medicament solution is available and $H^+$ or $OH^-$ produced during the iontophoresis procedure are constantly removed. As a direct result, pH within the system can be maintained within desired levels without the addition of buffers.

Figure 2:
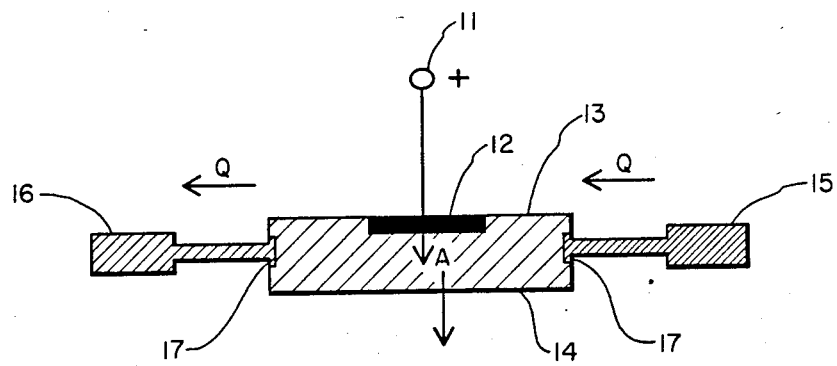
FIG. 2 is a schematic diagram of a flow-through electrophoresis electrode.

FIG. 2 is a diagramatic representation of such a flow-through electrode. A source of current is represented at 11, which is in turn placed in electrical communication with an electrode 12. The electrode 12 is, in turn, placed in communication with a reservoir or main drug compartment 13. One primary operative feature of the flow-through electrode system is that drug ions are driven from the main drug compartment 13, across the interface 14, in the general direction of arrow A by the electric current produced at the electrode. Interface 14 represents the interface or point of contact between the main drug compartment 14 and the patient.

Also placed in communication with main drug compartment 13 is a source chamber 15 which contains a continuous supply of solution containing medicament. An outlet chamber 16 is also placed in communication with main drug compartment 13. Membranes 17 can also be disposed between main drug compartment 13 and source chamber 15 and outlet chamber 16 to provide more control on the rate of flow through main drug compartment 13. Thus, fresh medicament solution can constantly be introduced into main drug compartment 13 and medicament solution containing undesirable produced ionic species can flow out of main drug compartment 13 into outlet chamber 16.

Solution introduced into the main drug compartment 13 could be obtained from different sources. Obviously, new fresh medicament solution could be used. In addition, solution which has already passed through the system into the outlet chamber 16 could be regenerated for recycling. Such solution could be regenerated by various methods including with the use of ion exchange resins.

Figure 3:
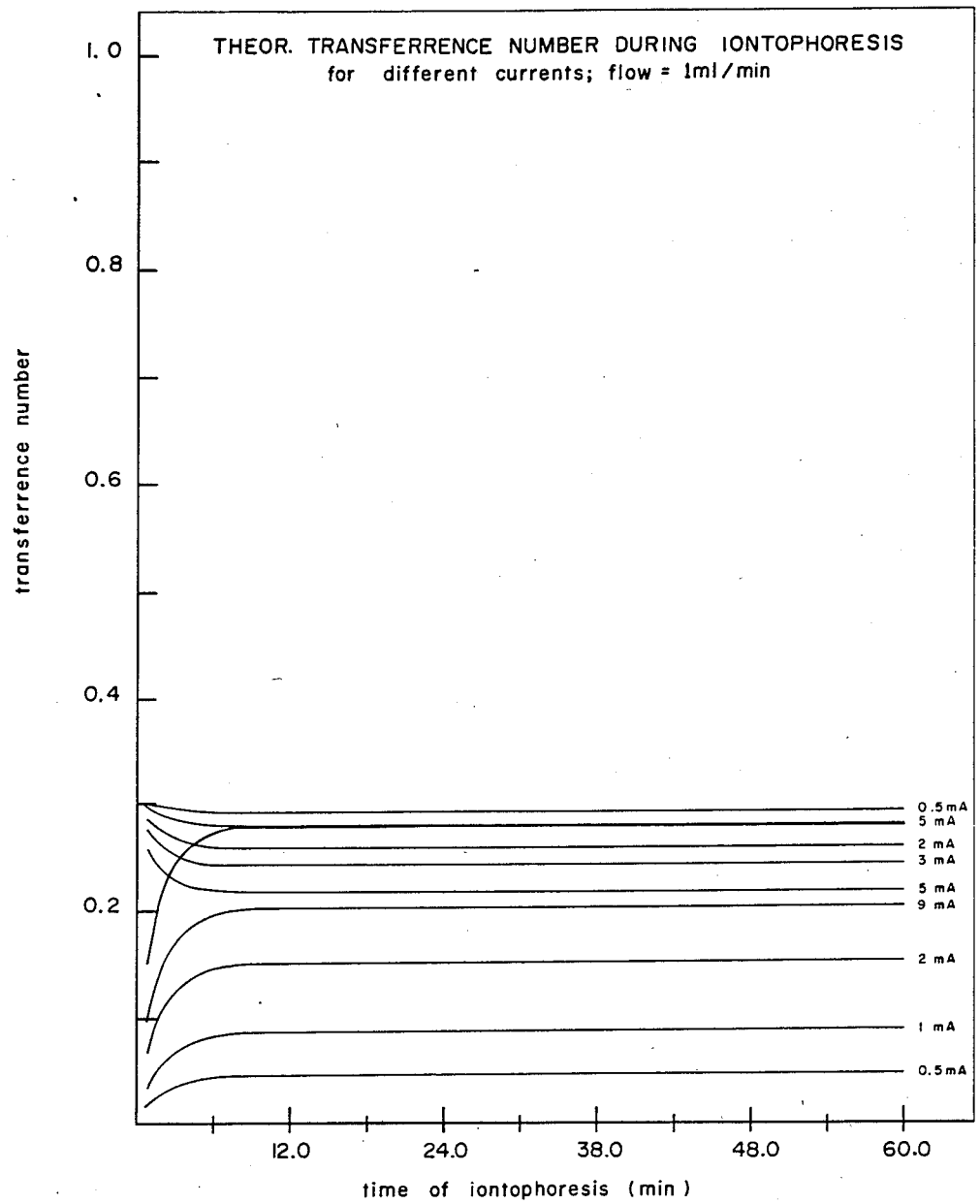
FIG. 3 is a graph indicating the theoretical transference numbers for a flow-through electrophoresis system for different currents.

FIG. 3 illustrates the theoretically transference number for different currents using a flow-through electrode. The theoretical transference numbers are calculated using the formulae set forth above. It should be noted that in each case the transference number quickly reaches a constant value.

Figure 4:
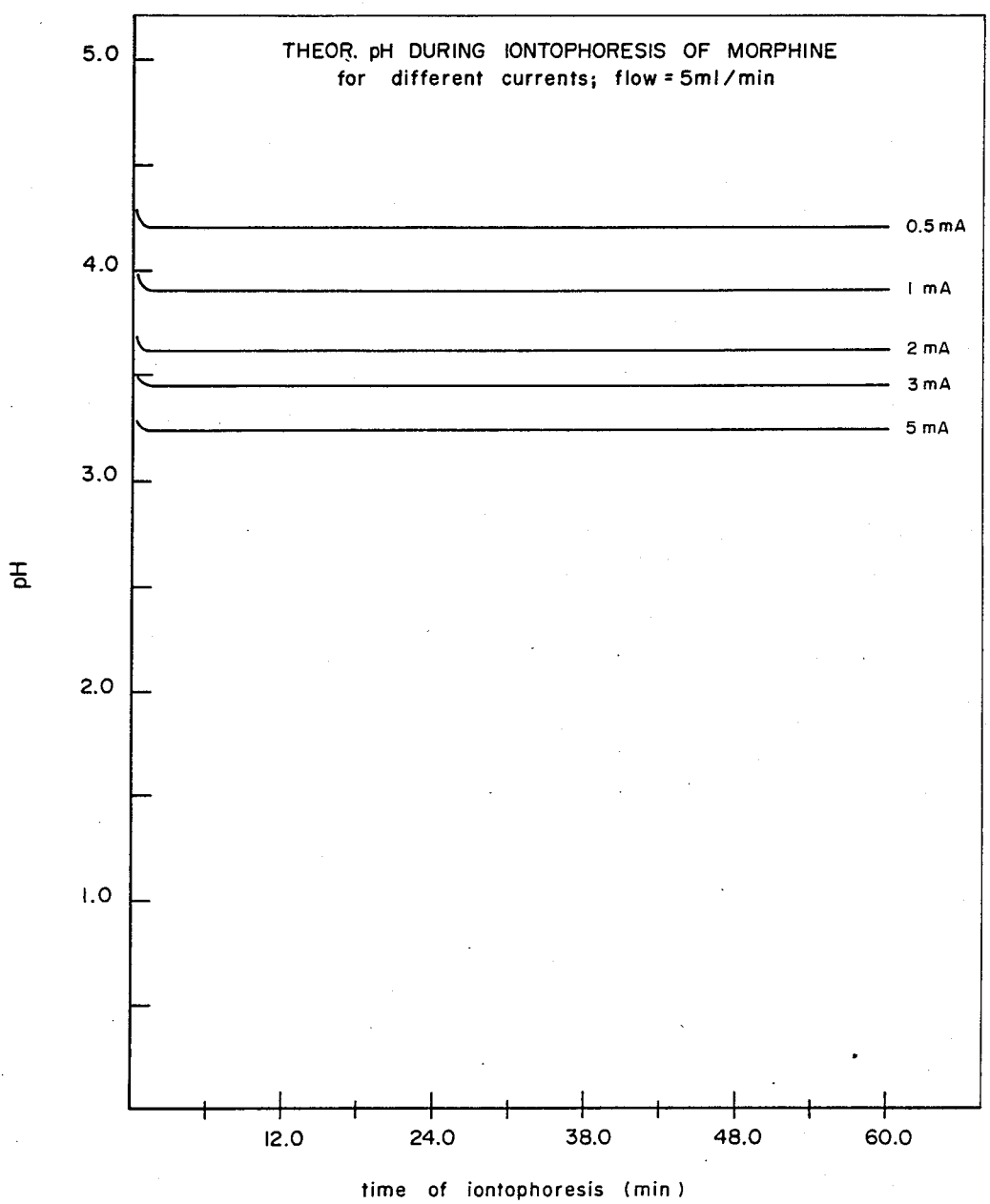
FIG. 4 is a graph indicating the theoretical pH for a flow-through electrophoresis system during morphine electrophoresis.

FIG. 4 illustrates the theoretical pH encountered in morphine iontophoresis using a flow-through electrode for several different currents. Again, it should be noted that the pH quickly achieves a constant value which is well within the safe range. Extremes in pH, such as those persistently found in conventional iontophoresis, are avoided.

Thus, it will be appreciated that all of the objects of the present invention can be achieved using the flow-through electrode. The amount of medicament introduced to the patient can be quantified because charge passing through the system is carried by medicament ions and not by buffer ions of products of the electrolysis of water. At the same time pH is maintained within desired limits in that $H^+$ and $OH^-$ ions produced in the system are readily removed.

D. Example

The following example is given to illustrate the general scope of the present invention. The example is not intended to limit the scope of the present invention.

EXAMPLE 1

An iontophoresis procedure within the scope of the present invention is performed for the purpose of administering morphine to a human patient. The drug is initially obtained in the form of sulfate in an aqueous solution having a concentration of about 10 mg/ml.

The medicament solution is introduced to the iontophoresis system through the use of a flow-through electrode. The flow-through electrode is configured wherein an electrode container is equipped with two additional ports, one being an inlet and the other being an outlet. Medicament solution is pumped at a flow rate of about 1 ml/min. through the electrode.

The iontophoresis system includes an inert electrode made out of stainless steel. Alternatively, glassy carbon could be used. The loaded medicament is introduced into the iontophoresis system into a solution of morphine sulphate which flows between the electrode and the skin of the patient. Current of about 2 mA is then passed through the system.

pH levels within such a system would be expected to be similar to those illustrated in FIG. 4.

The physiological reactions typically observed in the administration of morphine are demonstrated by the patients. These reactions includes the following: histamine release and decreased pupil size with diminished reaction to changing light conditions. Drug levels measured in the serum by radioimmunio assay technique indicate an increase of the drug concentration and correlated with the time of iontophoresis.

E. Summary

In summary, the present invention makes it possible to maintain pH at safe levels during the iontophoresis procedure. The use of the flow-through electrode is desirable where competing ions produced during the procedure required removal from the system. Thus, when employing the present invention, undesirable ions produced during the process are cleared from the iontophoresis medium at the same time desirable medicament ions are introduced into the medium.

The invention may be embodied in other specific forms without departing from its spirit or essential characteristics. The described embodiments are to be considered in all respects only as illustrative and not restrictive. The invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for iontophoretically administering a medicament through the skin of a patient while removing competing ions produced within the iontophoresis system by the electrolysis of water, the method comprising the steps of:
   (a) obtaining a first electrode and a second electrode;
   (b) obtaining a medium containing a medicament;
   (c) placing the first electrode in communication with the medium;
   (d) placing the medium in communication with the skin of the patient such that the medium is disposed between the first electrode and the skin of the patient;
   (e) placing the second electrode in communication with the skin of the patient at a point distal from the first electrode;
   (f) creating a voltage differential between the first and second electrodes such that the medicament is driven into the skin of a patient; and
   (g) simultaneously flowing fresh quantities of the medium containing medicament between the first electrode and the skin of the patient and removing quantities of the medium from between the first electrode and the skin of the patient which contain products of the electrolysis reaction of water while the voltage differential between the first and second electrodes exists, thereby iontophoretically administering a medicament through the skin of the patient while removing competing ions produced within the iontophoresis system by the electrolysis of water.

2. A method for iontophoretically administering a medicament as defined in claim 1 wherein fresh quantities of medium are continuously flowed between the first electrode and the skin of the patient.

3. A method for iontophoretically administering a medicament as defined in claim 1 wherein fresh quantities of medium are periodically flowed between the first electrode and the skin of the patient.

4. A method for iontophoretically administering a medicament as defined in claim 1 wherein fresh quantities of medium are flowed between the first electrode and the skin of the patient in response to changes in pH outside of a predetermined range.

5. A method for iontophoretically administering a medicament through the skin of a patient while simultaneously providing a continuous supply of fresh medicament and while removing medicament medium containing competing ions produced during iontophoresis, the method comprising the steps of:
   (a) obtaining a first electrode and a second electrode;
   (b) obtaining a iontophoresis medium containing a medicament;
   (c) placing the first electrode in communication with the iontophoresis medium;
   (d) placing the iontophoresis medium in communication with the skin of the patient such that the medium is disposed between the first electrode and the skin of the patient;
   (e) placing the second electrode in communication with the skin of the patient at a point distal from the first electrode;
   (f) providing means for flowing fresh medium between the first electrode and the skin of the patient and means for removing quantities of medium from between the first electrode and the skin of the patient which contain the products of the electrolysis reaction of water;

(g) creating a voltage differential between the first and second electrodes such that medicament ions are driven into the skin of the patient; and simultaneously (h) flowing fresh medium between the first electrode and the skin of the patient, and removing quantities of medium from between the first electrode and the skin of the patient which contain the products of the electrolysis reaction of water while the voltage differential between the first and second electrodes exists, such that the pH of the medium between the first electrode and the patient is maintained within a predetermined range.

6. A method for iontophoretically administering a medicament as defined in claim 5 wherein fresh medium is flowed constantly between the first electrode and the skin of the patient.

7. A method for iontophoretically administering a medicament as defined in claim 5 wherein fresh medium is flowed periodically between the first electrode and the skin of the patient.

8. A method for iontophoretically administering a medicament as defined in claim 5 wherein fresh medium is flowed between the first electrode and the skin of the patient when the pH of the medium leaves the predetermined range.

9. A flow-through electrode for use in iontophoresis comprising:
 an electrode;
 means for placing the electrode in communication with a source of electrical current;
 a drug compartment in communication with the electrode having an inlet through which iontophoresis medium containing a medicament enters said drug compartment and an outlet through which the iontophoresis medium exits said drug compartment;
 iontophoresis medium containing a medicament located within said drug compartment;
 means for forming an interface between the drug compartment and the skin of a patient such that medicament ions within the iontophoresis medium are capable of iontophoretic administration to the patient through said interface;
 means for passing iontophoresis medium containing medicament through the drug compartment while the interface between the drug compartment and the patient exists, thereby permitting the flow-through electrode to iontophoretically administer the medicament while simultaneously passing the iontophoresis medium through the drug compartment.

10. A flow-through electrode for use in iontophoresis as defined in claim 9, further comprising a source chamber in communication with the drug compartment such that iontophoresis medium can flow from the source chamber into the drug compartment through the drug compartment inlet.

11. A flow-through electrode for use in iontophoresis as defined in claim 10, further comprising an outlet chamber in communication with the drug compartment such that iontophoresis medium can flow from the drug compartment into the outlet chamber through the drug compartment outlet.

* * * * *

UNITED STATES PATENT AND TRADEMARK OFFICE
CERTIFICATE OF CORRECTION

PATENT NO. : 4,886,489

DATED : December 12, 1989

INVENTOR(S) : STEPHEN C. JACOBSEN et al.

It is certified that error appears in the above-identified patent and that said Letters Patent is hereby corrected as shown below:

Column 3, line 55, "whih cause" should be --which cause--
Column 4, line 9, "most of other ions," should be --most of the other ions,--
Column 7, line 67, delete "for"
Column 9, line 16, "th positive pole" should be --the positive pole--
Column 9, line 18, $H_2O \times O_2$" should be --$H_2O = O_2$--
Column 10, line 55, "theoretically" should be --theoretical--
Column 11, lines 44-45, "correlated" should be --correlate--
Column 12, line 52, "a iontophoresis" should be --an iontophoresis--

Signed and Sealed this

Tenth Day of December, 1991

*Attest:*

HARRY F. MANBECK, JR.

*Attesting Officer*  *Commissioner of Patents and Trademarks*